United States Patent
Koros et al.

[11] Patent Number: 5,944,658
[45] Date of Patent: Aug. 31, 1999

[54] LUMBAR SPINAL FUSION RETRACTOR AND DISTRACTOR SYSTEM

[76] Inventors: Tibor B. Koros; Gabriel J. Koros, both of 610 Flinn Ave., Moorpark, Calif. 93021

[21] Appl. No.: 08/935,761

[22] Filed: Sep. 23, 1997

[51] Int. Cl.$^6$ ............................................. A61B 17/02
[52] U.S. Cl. ........................... 600/232; 600/235; 600/231
[58] Field of Search ................................... 600/201, 217, 600/210, 231, 232, 233, 235

[56] References Cited

U.S. PATENT DOCUMENTS

| | | | |
|---|---|---|---|
| 1,706,500 | 3/1929 | Smith | 600/232 |
| 4,852,552 | 8/1989 | Chaux | 600/232 |
| 5,027,793 | 7/1991 | Engelhardt et al. | 600/235 X |
| 5,728,046 | 3/1998 | Mayer et al. | 600/210 |
| 5,755,660 | 5/1998 | Tyagi | 600/232 X |
| 5,788,630 | 8/1998 | Furnish | 600/232 |
| 5,795,291 | 8/1998 | Koros et al. | 600/235 X |

FOREIGN PATENT DOCUMENTS

| | | | |
|---|---|---|---|
| 963517 | 10/1982 | U.S.S.R. | 600/235 |

*Primary Examiner*—Jeffrey A. Smith
*Attorney, Agent, or Firm*—David O'Reilly

[57] ABSTRACT

A lumbar laminectomy retractor and distractor system comprised of a unique retractor system and unique distractor system. The retractor has one or more retractor frames including retractor blades for placement in an incision. The blades can be placed in an incision and then engaged by a retractor frame to spread the incision for viewing the surgical site. An optional, but preferred feature is a provision for tilting the retractor frame arms to spread the retractor blades, providing greater visualization of a surgical site. The distractor system has a distractor frame offset at right angles to the retractor frame, having fixed distractor blades, introduced into the incision and optionally held in place by screws, screwed into the vertebrae adjacent to the diseased or damaged disc. The screws are incorporated into the distractor blades on the distractor frame. The design of the retractor and distractor frames, with foldable crank arms, provide a low profile minimizing interference and allowing use of two or more retractors if desired.

21 Claims, 5 Drawing Sheets

LUMBAR SPINAL FUSION RETRACTOR AND DISTRACTOR SYSTEM

BACKGROUND OF THE INVENTION

1. Field of the Invention

This invention relates to retractors used in surgery and more particularly, relates to a lumbar spinal fusion retractor and distractor system includes screws or pins for attaching and holding a distractor in place on the spinal column.

2. Background Information

In surgical procedures, it is important that trauma to the patient, and damage to the tissue be minimized as much as possible. For that reason, surgeons try to keep incisions to a minimum when performing surgical procedures by making a mid-line mini-incision. However, the surgeon performing a delicate surgery must be able to have a clear view of the operating field. Various retractors are provided to keep an incision open and provide a clear view of the field of the operation.

Such surgical retractors are particularly important for performing spinal fusions, and particularly lumbar disc operation, where the surgical procedure is performed by an anterior/lateral approach through the abdomen. The surgeon makes a small incision in the abdomen and must be able to view the region of the vertebrae where the lumbar disc operation is to be performed. For this purpose, retractors are inserted in the incision to hold organs, muscles, arteries and other tissue out of the way, and provide a clear view of the spinal region being turned on.

It is also important that the retractor permits insertion of retracting blades without damage to the tissue. To do this, the retractor is constructed to only displace a small volume when inserted in the incision before is opened, or "spread" to provide a clear view of the operating field.

It is also important that the retractor stay in position during this difficult procedure. If the retractor should slip during the surgical procedure, this can cause additional trauma to the surrounding tissue and further delays in the operating procedure. Such surgical procedures should be completed efficiently and as quickly as possible to avoid ischemia and necrosis of the surrounding tissue, and also to minimize the time the patient is kept under anesthesia.

It is therefore, one object of the present invention to provide a lumbar laminectomy retractor and distractor that provides a clear field of view of an operation site.

Still another object of the present invention is to provide a lumbar fusion retractor/distractor system that is firmly held in place after insertion in a patient.

Yet another object of the present invention is to provide a lumbar fusion/laminectomy retractor and distractor or corpectomy retractor system that has temporary screws or pins for attaching distractor blades to adjacent vertebrae.

Still another object of the present invention is to provide a lumbar laminectomy retractor and distractor system having blades that can be spread by tilting arms on a retractor frame.

Other objects, advantages and novel features of the invention become apparent from the following detailed description when considered in conjunction with the accompanying drawings or like reference numbers identified like parts throughout.

BRIEF DESCRIPTION OF THE INVENTION

The purpose of the present invention is to provide an improved lumbar fusion/laminectomy retractor and a distractor that can be fixed in place for attachment to vertebrae of the spine by screws or pins to spread adjacent vertebrae, and provide a clear view of the field of operation while minimizing the size of an incision and the trauma to the surrounding tissue.

The lumbar fusion retractor and distractor system of the present invention is comprised of a retractor frame and distractor frame, each having a pair of parallel arms attached on opposite ends of a cross arm that includes a rack gear. One arm is fixed on the first end of the crossbar, while the other arm is movable along the rack gear for fine adjustment of the arms. A pinion gear engaging the rack gear is turned by a foldable crank handle to close or open the parallel arms. The connection of the retractor and distractor frames, with foldable crank arms, provides a low profile to minimize interference with the surgeon performing the surgical procedure.

A unique feature of the invention is the provision of blades on the distractor that optionally include temporary screws or pins. The screws or pins slide into lengthwise channels in the distractor blades for receiving the screws that at the surgeons option, can be attached to adjacent vertebrae to hold the distractor firmly in place and carefully spread or distract adjacent vertebrae during operation on an intervertebral disc. The distractor frame is carefully positioned in the incision with a clamp handle, and screws are screwed into adjacent vertebrae. The distractor blades are then engaged by adjustable distractor frame arms.

The lumbar retractor and distractor system is carefully positioned by first placing the blades in the incision, on opposite sides of the spine, chosen according to patient requirement. A clamp handle clamps on a retractor blade to allow manual insertion and positioning of a blade. This allows hand retraction before introducing the retractor frame. With the blades positioned, or placed in a standard mid-line incision a retractor frame, comprised of a crossbar, having a rack gear and a pair of arms normal to the crossbar is introduced. One retractor arm is positioned on the end of the crossbar while the other arm is movable to open or close the retractor arms and spread the retractor blades.

The retractor arms are positioned fully closed between the heads of the retractor blades and cranked open until the blades become engaged with notches or slots in the end of the retractor arms. The retractor arms are then opened further until the desired position is achieved, and a clear view of the operating site is obtained. The heads of the blades will self-engage and self-lock in the slots in the end of the retractor arms and are held firmly in place by tissue pressure. The clamp handle may then be removed. Once the surgeon has a clear view of the operating site by positioning the blades and opening the retractor arms, a distractor at right angles to the retractor, can be introduced.

The second distractor has blades that include screws or pins. The surgeon can place these blades in the incision in the cephalad-caudad direction with a clamp handle. Screws that slide down a channel in each blade are then screwed into adjacent vertebrae on opposite sides of the lumbar disc being turned on. Pilot holes may be drilled in the vertebrae to ease the insertion of the fixation screws. Once these blades are positioned and pinned in place, a second offset frame can be introduced to engage the heads of the distractor blades. The adjacent vertebrae can be spread by gently cranking the right angle offset distractor frame to spread the firmly attached distractor.

The field of view can then be widened by using a tilt mechanism to spread the tips of the blades on the retractor to retract surrounding tissue without enlarging the incision. In this position, the surgeon will have a clear view of the lumbar disc region.

The sequence of installing the retractor and distractor blades and frames, of course, may vary. Generally, the retractor blades will be installed first to provide a clear view of the operating field before the distractor blades are attached to the vertebrae.

The above and other novel features of the invention will be more fully understood from the following detailed description and the accompanying drawings, in which:

DETAILED DESCRIPTION OF THE INVENTION

Figure 1:
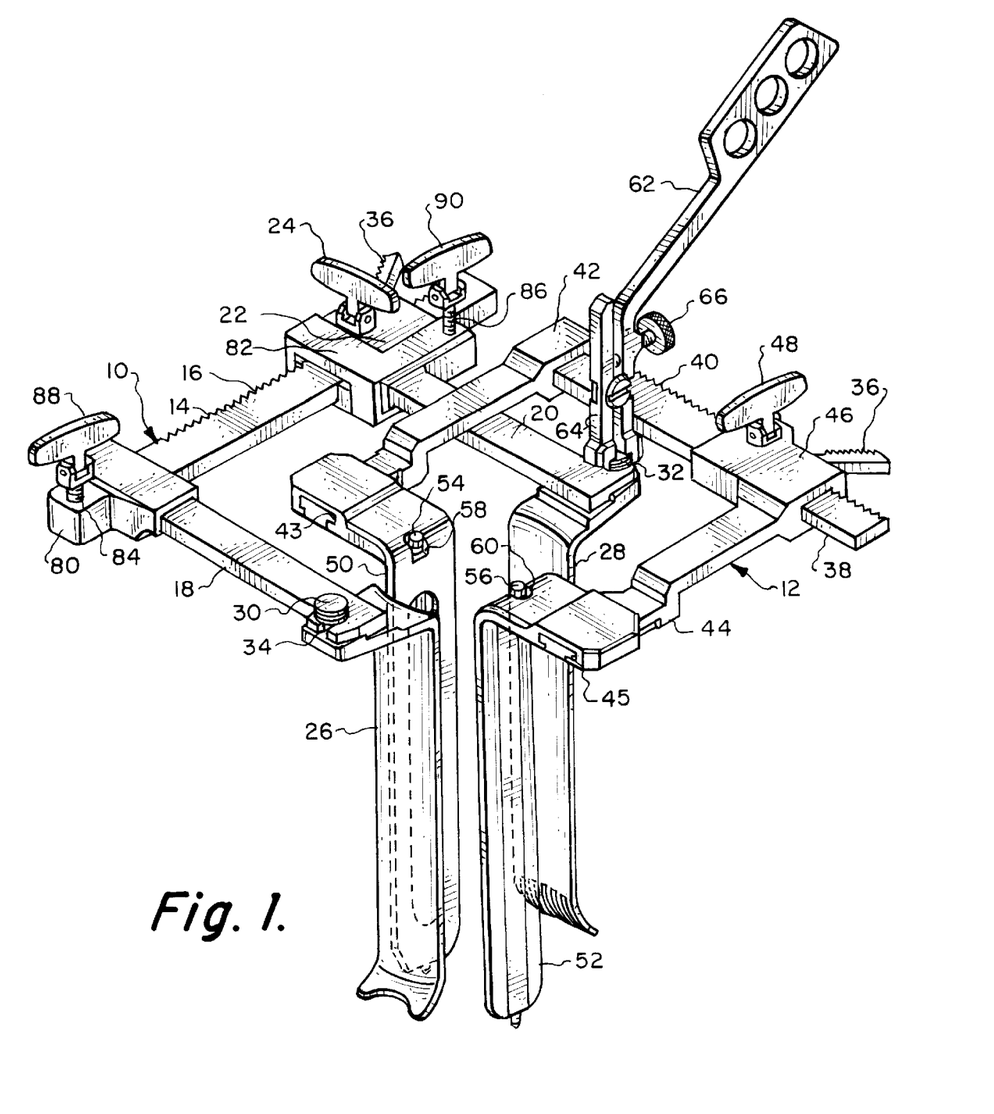
FIG. 1 is an isometric view of a lumbar laminectomy retractor and distractor system according to the invention.

A lumbar laminectomy retractor and distractor system is generally shown in FIG. 1. The lumbar fusion/laminectomy retractor and distractor system is comprised of a retractor frame 10 and a distractor frame 12 offset at right angles to the retractor frame. The lumbar retractor frame 10 is designed to be placed in an incision and spread to open the incision for viewing and placing lumbar distractor frame 12.

Lumbar laminectomy retractor frame 10 is comprised of a crossbar 14, having a rack gear 16 with left and right arms 18 and 20 normal to crossbar 14. Retractor arm 18 is securely attached to the end of crossbar 14. Second retractor arm 20 is mounted on a movable housing 22, having a foldable crank arm 24 for operating a pinion gear (not shown) engaging rack gear 16. Rotation of crank handle 24 operates the pinion gear and moves second arm 20 toward or away from fixed arm 18. While the drawing shows the fixed arm on the left side of crossbar 14, it should be realized that the fixed arm and movable arms can be reversed.

Multiple retractor frames 10 (2 or 3) may be used if desired. For multi-level fusion procedures one or more additional retractor frames can be introduced. Additional frames can be offset with longer blades used if desired.

Fixed retractor arm 18 and movable retractor arm 20 support retractor blades 26 and 28, having blade heads 30 and 32 engaging notches or slots 34 in the ends of respective retractor arms 18 and 20 as is well known in the art, and will be described in greater detail hereinafter. Retractor frame 10 includes spring loaded releasable arm lock 36 that holds movable arm 20 in place after the retractor has been properly positioned. Arm lock 36 prevents movable arm 20 from moving unless lock 36 is pressed toward rack gear 16, releasing pinion gear housing 22. Releasing arm lock 36 prevents movement of retractor arm 20.

Distractor frame 12 is also comprised of a crossbar 38, having rack gear 40 and a right or left fixed arm 42 and movable arm 44. Fixed arm 42 is securely attached to one end of crossbar 40, while movable arm 44 is attached to pinion gear housing 46 having foldable crank arm 48 for repositioning movable arm 44 on crossbar 38. Both crank arms 24 and 48 are mounted on pivot pins allowing them to be folded flat against the pinion gear housings 22 and 46, after the retractor and distractor frames 10 and 12 have been positioned. Thus, both retractor and distractor present a low profile when installed.

A unique feature of the invention is the inclusion of distractor blades 50 and 52, having screws 54 and 56. Screws 54 and 56, on retractor blades 52 and 54 slide into lengthwise channels or slots 58 and 60. Screws 54 and 56, are fed through lengthwise slots 58 and 60, in blades 50 and 52, and firmly hold distractor frame 20 and blades 50 and 52 in place with adjacent vertebrae spread or distracted during operation on a lumbar disc. Lumbar spinal fusion distractor frame 12 also includes a spring loaded releasable lock 36 that locks movable arm 44 and pinion gear housing 46 in a set position. To move arm 44, lock 36 must be pressed toward crossbar 38 allowing arm 44 to be moved by operation of crank handle 48 to turn a pinion gear (not shown) in housing 42 engaging rack gear 40.

Retractor blades 26 and 28 are carefully positioned by hand placed in an incision by clamp handle 62, having clamping lever 64 to clamp on head 30 and 32 of the respective blades 26 and 28. Thumbscrew 66 locks lever 64 on the blade head. Blade insertion clamp handle 62 allows blades 26 and 28 to be carefully positioned by hand in an incision before engagement by retractor frame 10.

Figure 2:
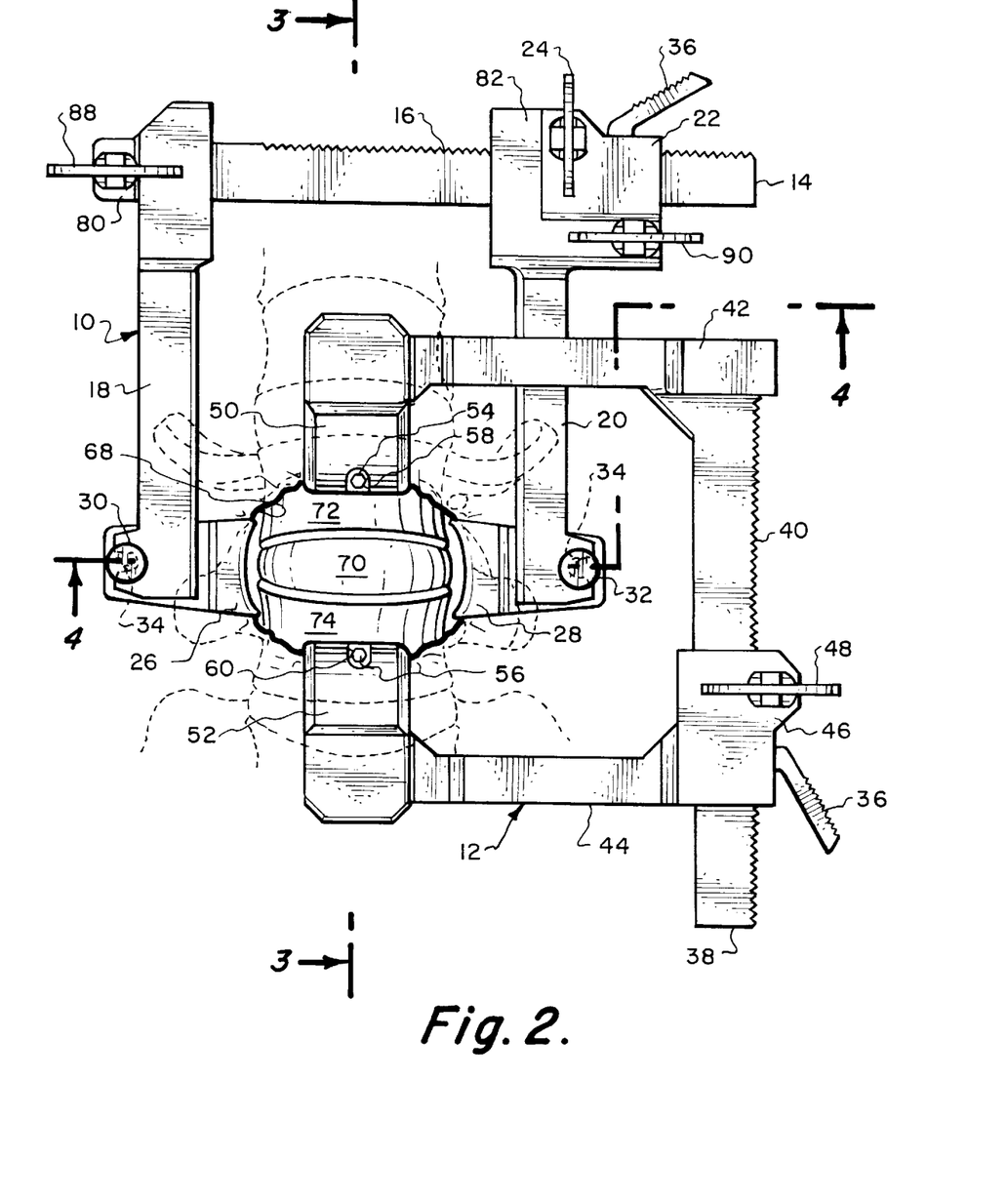
FIG. 2 illustrates the placement of the lumbar laminectomy retractor system in an incision for distracting adjacent vertebrae during operation on a defective lumbar disc.

The lumbar retractor and distractor system of the present invention is shown positioned for a surgical procedure in FIG. 2. The retractor and distractor system is positioned in an incision 68 to provide a clear view of a diseased or defective lumbar disc 70. Retractor frame 10, with blades 26 and 28 are positioned in incision 68 to spread the incision for placement of fixed retractor frame 12, as will be described in greater detail hereinafter.

Retractor blades 26 and 28 are carefully placed in incision 68 by clamp handle 62 traverse to the spine. Retractor frame 10, in a fully closed position, is then placed between retractor blade heads 30 and 32, and opened by operating crank handle 24 until notches 34 in the ends of retractor arms 18 and 20 engage heads 30 and 32. Clamp handle 62 may then be removed and retractor 10 opened further by turning crank handle 24 until the desired position is obtained. Offset distractor frame 12 is then positioned in incision 68 with screws 54 and 56 screwed into adjacent vertebrae 72 and 74 on opposite sides of disc 70. Screws 54 and 56 hold offset retractor frame 12 firmly in position allowing adjacent vertebrae 72, 74 to be spread providing a clear view of the operating site.

Figure 3:
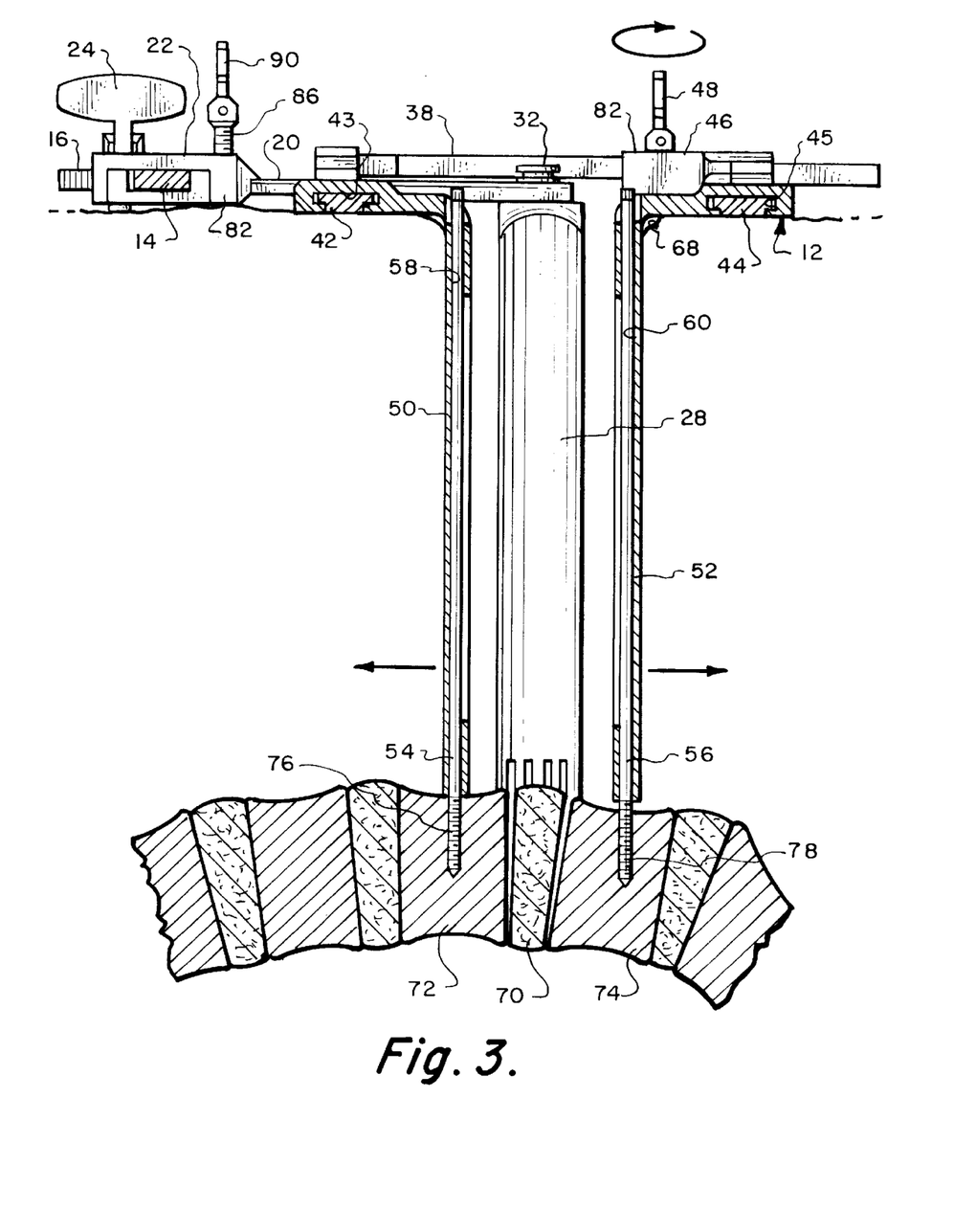
FIG. 3 is a sectional view taken at 3—3 of FIG. 2.

The positioning and placement of distractor frame 12, offset at right angles to retractor frame 10, is shown in FIG. 3. After retractor frame 10 is positioned in incision 68, fixed distractor blades 50 and 52 can be positioned with distractor 16 frame 12, by installing screws 54 and 56 into adjacent vertebrae 72 and 74. Distractor blades 50 and 52 are carefully positioned by hand over vertebrae 72 and 74 also with a clamp handle 62. Screws 54 and 56 slide down channels 58 and 60, and are screwed into pilot holes 76 and 78 in adjacent vertebrae 72 and 74 (FIG. 2) firmly holding distractor blades 50 and 52 in position. Distractor frame 12 can then be introduced between distractor blades 50 and 52 with the end of arms 42, 44 engaging sockets 43, 45 in distractor blades 50, 52. Clamp handle 62 may then be removed and crank 48 gently cranked to spread distraction blades 50, 52 spreading adjacent vertebrae 72, 74 for treating diseased or defective disc 70.

Figure 4:
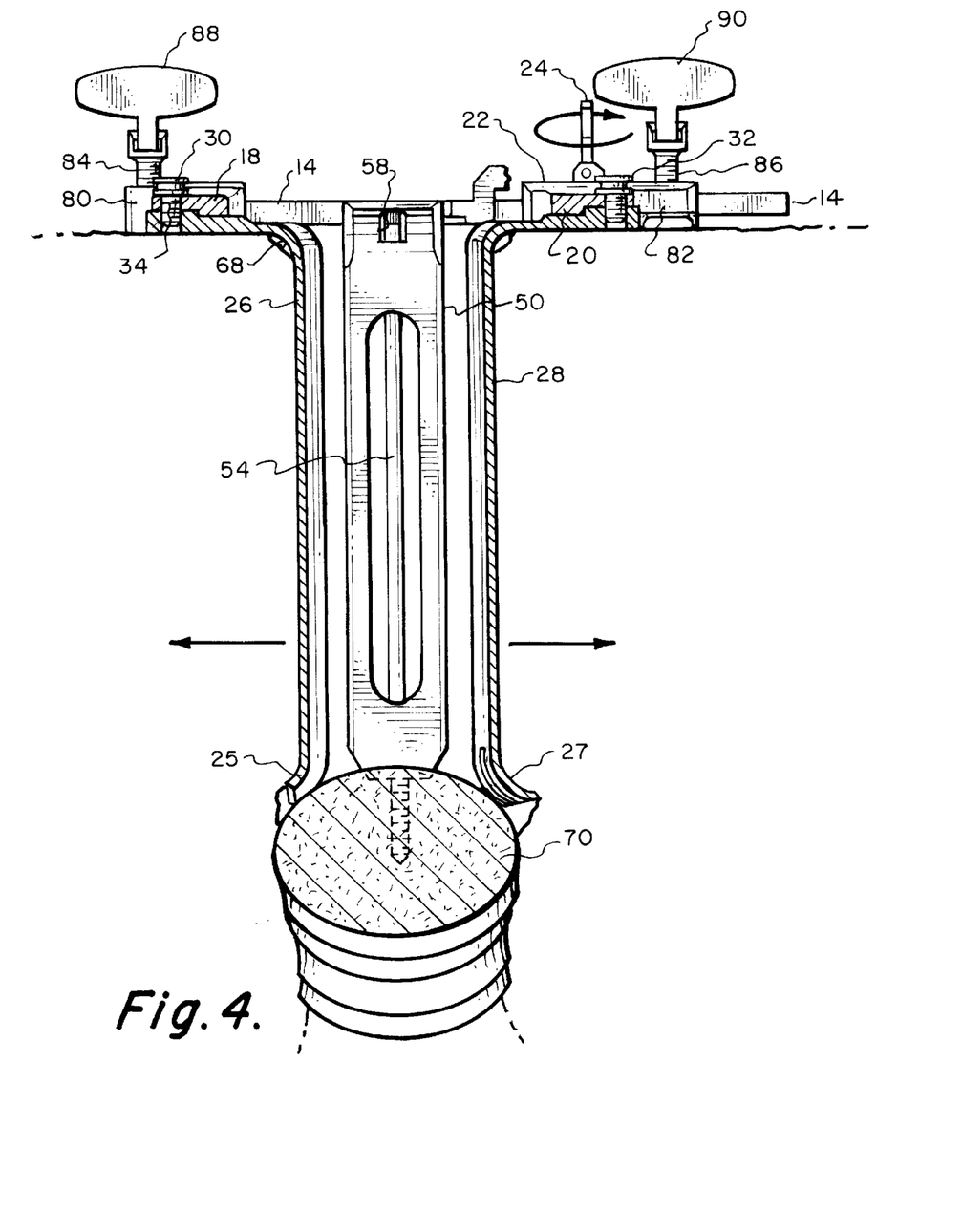
FIG. 4 is a sectional view taken at 4—4 of FIG. 2.
Figure 5:
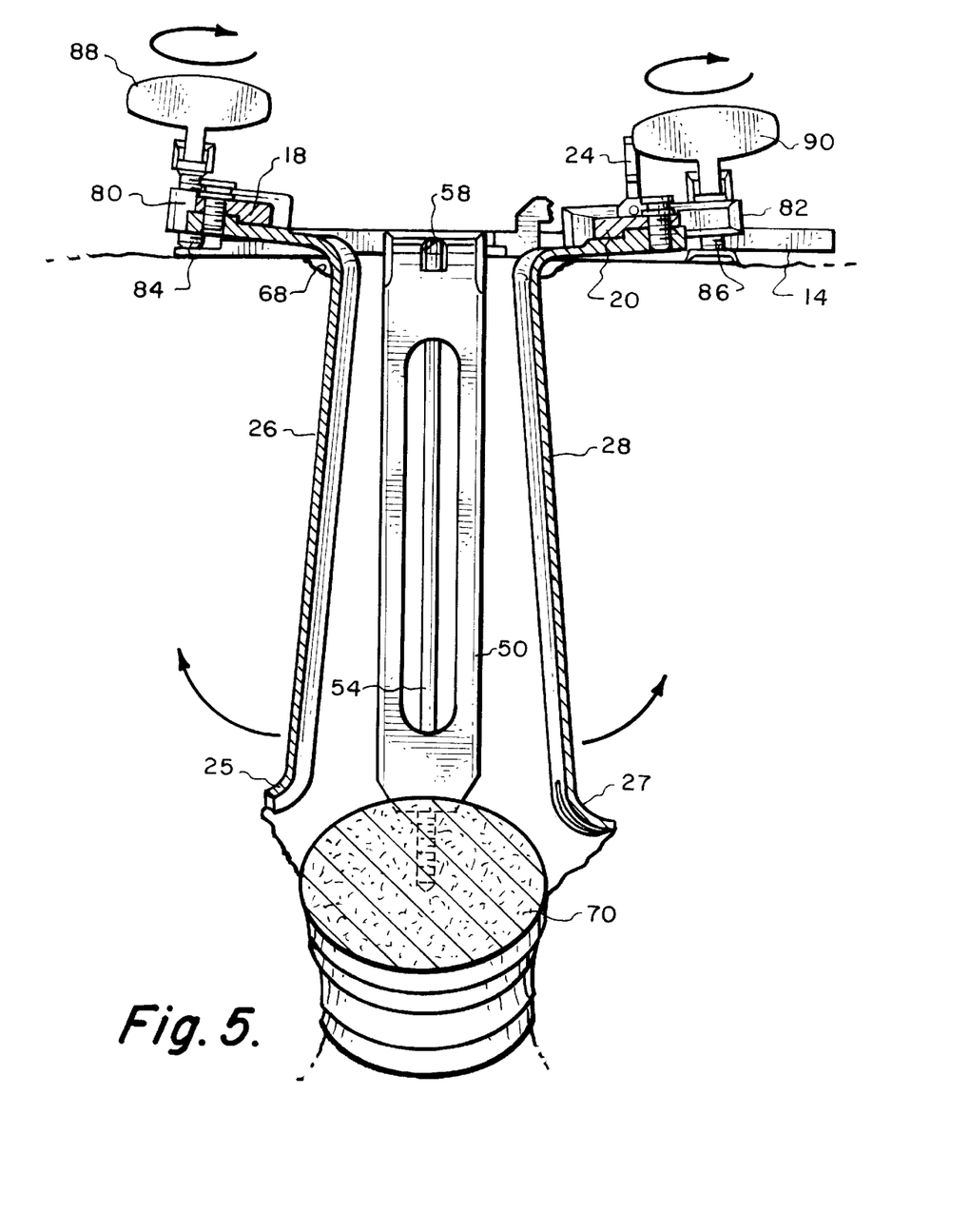
FIG. 5 illustrates the mechanism for spreading the retractor blades.

An optional, but preferred feature of the invention is the ability to enlarge the view of the operating site without increasing or spreading incision 68. This optional improvement is illustrated in FIGS. 4 and 5. The optional embodiment allows retractor blades 26 and 28 to be spread by tilting them to widen their retraction angle, without increasing the size of the incision. This allows retractor blades 26 and 28 to carefully retract patient tissue with minimum trauma.

Arms 18 and 20, of retractor frame 10 (FIG. 1) are mounted on couplings 80 and 82, to allow arms 18 and 20 and therefore, retractor blades 26 and 28, to be tilted, spreading the inner ends or tips 25 and 27 respectively to increase the view of the damaged or diseased disc 70. The tilting mechanism is comprised of threaded shafts 84 and 86, having foldable crank handles 88, 90 passing through couplings 80 and 82 with their ends engaging crossbar 14. Other optional tilt mechanism, that would work equally as well are a ratchet mechanism or a grooved shaft mechanism. To tilt ends 25 and 27 of retractor blades 26 and 28 away from the spine and damaged disc 70, crank handles 88 and 90 are rotated clockwise as shown. This extends threaded shafts 84 and 86 to tilt couplings 80, 82, tilting arms 18 and 20, and therefore, spreads or tilts retractor blades 26 and 28. Retractor blades 26 and 28 can be tilted before or during the surgical procedure to enlarge the viewing area. While threaded shafts 84 and 86 are shown to provide blade tilt, other mechanisms might be used. For example, a ratchet mechanism could be used to tilt retractor blades 26 and 28.

Preferably, retractor blades 26 and 28 would be placed in incision 68, engaged by arms 18 and 20 to spread the incision by turning crank handle 24 until a desired position is obtained. Crank handles 88 and 90 could then be turned to tilt retractor arms 26, 28 spreading retractor arm tips 25 and 27, increasing the viewing area and making it easier to place fixed blades 50 and 52. This will provide the surgeon a clear view of the adjacent vertebrae 72,74 for placing of fixation screws 54 and 56, or for drilling holes for their placement.

To use the system, retractor blades 26 and 28, of retractor frame 10, are positioned in incision 68 using clamping handle 62 Once retractor blades 26 and 28 are in position in the incision adjacent the surgical site, they are held in a parallel position slightly retracting lateral tissue. Retractor frame 10 can be a left or right retractor frame chosen according to the patient's position or both according to the number of levels. Retractor frame arms 18 and 20 are closed sufficiently to allow the ends of retractor arms 18 and 20 to fit between blade heads 30 and 32 on retractor arms 26 and 28. Retractor frame 10 is then slightly opened by operation of crank arm 24, until notches 34 at the ends of retractor arms 18 and 20 engage retractor blade heads 30 and 32. Crank handle 24 is then turned clockwise until the proper retraction of incision 68, providing a sufficiently clear view of lumbar disc 70 is obtained.

Distractor blades 50, 52 are introduced and carefully positioned by hand with clamp handle 62 over adjacent vertebrae 72, 74. Screws 54 and 56, slide through channels 58, 60, in distractor blades 50, 52 and are screwed into predrilled holes in adjacent vertebrae 72 and 74, firmly holding distractor blades 50, 52 in place. Offset retractor frame 12 in then positioned at right angles to retractor frame 10 with the ends of distractor arms engaging the ends of distractor blades 50, 52. Rotation of crank handle 48 gently spreads or distracts vertebrae 72, 74 for operating on diseased or defective disc 70. A clear view of the operation site is provided by the mechanism that allows retractor blades 26 and 28 to be tilted to carefully retract tissue adjacent to the spine without increasing the size of incision 68. Increased viewing area makes it possible to more easily install screws 54 and 56, and fixed distractor blades 50 and 52. Additional retractor blades and tilt frame can be used if desired. An additional retractor could be positioned, for example, at about 45° to the first retractor 10 between retractor 10 and distractor 12. The system may be secured with flexible instrument holders to the surgical table for added stability and safety if desired.

Thus, there has been disclosed an improved lumbar laminectomy retractor and distractor system, comprised of a pair of mutually offset retractor frames. A retractor frame having retractor blades that may be positioned in the incision and spread, but also may be tilted so that the blade ends or tips, follow the contour of the spine, may retract adjacent tissue and arteries to provide a wide view of the surgical site. A distractor frame, offset 90° from the retractor frame, includes fixed distractor blades, secured to adjacent vertebrae opposite the damaged or diseased disc by screws or pins screwed into predrilled holes. This provides the surgeon, performing a surgical procedure such as a discectomy, a clear view of the operating site with a small incision. This is a great benefit to the patient because it makes the surgical procedure easier, reduces trauma to surrounding tissue and promotes healing because the incision is kept to a minimum.

This invention is not to be limited by the embodiment shown in the drawings and described in the description which is given by way of example and not of limitation, but only in accordance with the scope of the appended claims.

What is claimed is:

1. A lumbar spinal fusion retractor and distractor system comprising;

a retractor frame having parallel arms extending perpendicular to a crossbar, one of said arms being movable toward or away from the other;

a pair of retractor blades removably held movably and freely engaging free ends of said pair of parallel arms for spreading and retracting a surgical incision;

a distractor frame having parallel arms extending perpendicular to a crossbar, one of said parallel arms being movable toward or away from the other;

a pair of distractor blades engaging free ends of said parallel arms;

fastening means for fastening said pair of distractor blades to adjacent vertebra;

whereby said distractor frame and pair of distractor blades are firmly held in place on a spinal column to provide a clear view and distraction of an operating site.

2. The system according to claim 1 including means for spreading tips on said pair of retractor blades after placement in an incision and engagement with said arms on said first frame.

3. The system according to claim 2 in which said means for spreading tips of said pair of retractor blades comprises means for tilting said pair of retractor blades.

4. The system according to claim 3 in which said means for tilting said pair of retractor blades comprises means for tilting said parallel arms with said retractor blades engaged.

5. The system according to claim 4 in which said means for tilting said parallel arms comprises; coupling means coupling said parallel arms to said crossbar; angle adjusting means for adjusting the angle of said parallel arms with respect to said crossbar.

6. The system according to claim 5 in which said angle adjusting means comprises; a threaded shaft passing through said coupling on each of said parallel arms; a handle on an end of said threaded shaft; whereby rotation of said handles causes said coupling to tilt thereby tilting the respective parallel arm and retractor blade.

7. The system according to claim 6 in which said fastening means comprises screws.

8. The system according to claim 7 in which said screws are incorporated in said pair of distractor blades.

9. The system according to claim 8 in which said pair of distractor blades each have a lengthwise channel; said screws being retained in a respective lengthwise channel.

10. The system according to claim 1 in which said fastening means comprises screws.

11. The system according to claim 10 in which said screws are incorporated in said pair of distractor blades.

12. The system according to claim 11 in which said pair of distractor blades each have a lengthwise channel; said screws being retained in a respective lengthwise channel.

13. A lumbar laminectomy retractor system comprising;
 a retractor frame having parallel arms extending perpendicular to a crossbar, one of said arms being movable toward or away from the other; said parallel arms having first ends attached to said cross bar and free ends;
 a pair of retractor blades engaging free ends of said pair of parallel arms for spreading and retracting a surgical incision;
 tilting means for tilting said retractor blades;
 tilt adjusting means for continuously and independently adjusting a tilt angle of each of said retractor blades respectively after placement of said retractor frame;
 whereby the field of view during a surgical procedure can be enlarged by tilting said retracting blades.

14. The system according to claim 13 in which said tilt adjusting means comprises means for spreading tips on said pair of retractor blades after placement in an incision and engagement with said arms on retractor frame.

15. The system according to claim 14 in which said tilt adjusting means for tiling said pair of retractor blades comprises means for tilting said parallel arms with said retractor blades engaged.

16. The system according to claim 15 in which said means for tilting said parallel arms comprises; coupling means coupling said parallel arms to said crossbar; angle adjusting means for adjusting the angle of said parallel arms with respect to said crossbar.

17. The system according to claim 16 in which said angle adjusting means comprises; a threaded shaft passing through said coupling means on each of said parallel arms; a handle on an end of said threaded shaft; whereby rotation of said handles causes said coupling to tilt thereby tilting the respective parallel arm and retractor blade.

18. A lumbar laminectomy distractor system comprising;
 a distractor frame having parallel arms extending perpendicular to a crossbar, one of said arms being movable toward or away from the other;
 a pair of distractor blades for engaging free ends of said parallel arms;
 fastening means for fastening said pair of distractor blades to adjacent vertebra;
 open-ended longitudinal guide means in said pair of distractor blades for receiving said fastening means;
 whereby said fastening means may be passed through said open-ended longitudinal guide means after placement of said distractor so that said distractor frame and pair of distractor blades are firmly held in place on a spinal column to provide a clear view of an operating site.

19. The system according to claim 18 in which said fastening means comprises screws.

20. The system according to claim 19 in which said screws are incorporated in said pair of distractor blades.

21. The system according to claim 20 in which said longitudinal guide means in said pair of distractor blades is a lengthwise channel; said screws being retained in a respective lengthwise channel.

* * * * *

UNITED STATES PATENT AND TRADEMARK OFFICE
CERTIFICATE OF CORRECTION

PATENT NO. : 5,944,658
DATED : August 31, 1999
INVENTOR(S) : Tibor B. Koros; Gabriel J. Koros It is certified that error appears in the above-identified patent and that said Letters Patent is hereby corrected as shown below:

```
Column 4, line 11, delete "frame 20" and insert
          -- frame 12 --;
          line 58, delete "(Fig. 2)" and insert
          -- (FIG. 3) --;
Column 5, line 16, before "grooved shaft mechanism"
          insert -- gear-like --;
Column 8, line 1, Claim 16, after "in which said"
          insert -- tilt-adjusting --.
```

Signed and Sealed this

Eleventh Day of July, 2000

Attest:

Q. TODD DICKINSON

*Attesting Officer*      *Director of Patents and Trademarks*